United States Patent
Hahn et al.

(10) Patent No.: US 6,806,044 B2
(45) Date of Patent: Oct. 19, 2004

(54) METHOD OF MEASURING CERULOPLASMIN CONCENTRATION IN A BLOOD SPOT, KIT AND METHOD OF DIAGNOSING WILSON'S DISEASE

(75) Inventors: Si-Houn Hahn, Kyungkyi-Do (KR); Young-Ju Jang, Kyungkyi-Do (KR); Soo-Young Lee, Kyungkyi-Do (KR); Ha-Cheol Shin, Kyungkyi-Do (KR); Sun-Young Park, Kyungkyi-Do (KR); Eun-Sun Yu, Kyungkyi-Do (KR); Hee-Sung Han, Seoul (KR)

(73) Assignee: Zenovac, Inc., Suwon-Si (KR)

( * ) Notice: Subject to any disclaimer, the term of this patent is extended or adjusted under 35 U.S.C. 154(b) by 370 days.

(21) Appl. No.: 09/965,126

(22) Filed: Sep. 26, 2001

(65) Prior Publication Data

US 2002/0142360 A1 Oct. 3, 2002

(30) Foreign Application Priority Data

Mar. 31, 2001 (KR) .................................. 10-2001-17100

(51) Int. Cl.[7] .............................. C12Q 1/00; C12Q 1/26; C12Q 1/28; G01N 33/53
(52) U.S. Cl. .............................. 435/4; 435/25; 435/975; 435/28
(58) Field of Search .............................. 435/4, 25, 975, 435/28

(56) References Cited

U.S. PATENT DOCUMENTS 5,491,066 A * 2/1996 Hiyamuta et al. ............ 435/7.4

6,010,903 A 1/2000 Hiyamuta et al. .......... 435/338

FOREIGN PATENT DOCUMENTS

EP  0 606 516 A1  7/1994
JP  8-75743  3/1996

OTHER PUBLICATIONS

Nakamura et al,"J.Biol.Chem.",V270(13),pp7656–60(Mar. 19995)(Abstract Only).*
Yamaguchi, et al., "Mass Screening for Wilson's Disease: Results and Recommendations," *Pediatrics International*, vol. 41, 1999, pp. 405–408.
European Search Report for European application No. EP 01 30 8243, dated Aug. 6, 2002.
Ohura, et al., "Pilot study of screening for Wilson disease using dried blood spots obtained from children seen at outpatient clinics" 1994, J. Inher. Metab. Dis. 22, pp. 74–80.
Hiyamuta, et al., :Monoclonal Antibody Against the Active Site of Caeruloplasmin and the ELISA System Detecting Active Caeruloplasmin 1994, Hybridoma, vol. 13(2), pp. 139–141.

* cited by examiner

*Primary Examiner*—Louise N. Leary
(74) *Attorney, Agent, or Firm*—Knobbe, Martens, Olson & Bear LLP

(57) ABSTRACT

The present invention relates to a method for measuring a holoceruloplasmin concentration, and more particularly, to a method for measuring a holoceruloplasmin in a blood spot based on a standard concentration curve obtained through an enzyme-linked immunosorbent assay (ELISA) or a dissociation-enhanced time-resolved fluoroimmunoassay using a holoceruloplasmin-specific polyclonal antibody and a holoceruloplasmin-specific monoclonal antibody.

29 Claims, 2 Drawing Sheets

METHOD OF MEASURING CERULOPLASMIN CONCENTRATION IN A BLOOD SPOT, KIT AND METHOD OF DIAGNOSING WILSON'S DISEASE

This application claims priority of KR 10-2001-0017100, filed Mar. 31, 2001.

BACKGROUND OF THE INVENTION

1. Field of the Invention

The present invention relates to a method for measuring holoceruloplasmin concentration. More specifically, the present invention relates to a method for measuring holoceruloplasmin concentration on a blood spot using a standard curve of concentration obtained through an enzyme-linked immunosorbent assay (ELISA) or a dissociation-enhanced time-resolved fluoroimmunoassay using a specific polyclonal antibody and a monoclonal antibody of the holoceruloplasmin.

The method for measuring holoceruloplasmin concentration on a blood spot is very useful for screening of Wilson's disease in population.

2. Description of the Related Art

It was back in 1912 when Wilson's disease was known to the public for the first time. Now, one in 25,000 to 30,000 people is suffering from an autosomal recessive disease, one of common genetic diseases with a carrier rate of 1/90. Wilson's disease is copper metabolism defect, that is, copper is not easily excreted through a biliary nor is incorporated into ceruloplasmin. Therefore, copper gets precipitated in the liver, brain, cornea, red blood cell and kidney, causing hepatic dysfunction including hepatitis, liver cirrhosis, neurologic disturbance like dysarthria, hemolytic anemia or renal tubular dysfunction, etc.

Unfortunately, most patients with Wilson's disease are diagnosed after liver cirhoisis or neurologic damage already developed. Although liver transplantation is available, many of them suffer to die or live with severe neurologic sequelae. However, if the diagnosis is made at an early stage of clinical course, they can have normal life back by starting an early treatment with an orally applied chelating agent, e.g., D-phenicillamine or trienthylene tetramine, without any further complications. Therefore, early diagnosis and treatment is very important to Wilson's disease.

One of the most valuable indexes to diagnose Wilson's disease is level of cerulaplasmin in blood. Ceruloplasmin has a molecular weight of 132,000 and 6–7 atoms of copper per molecule. Normally, ceruloplasmin is plasma protein and contains 95% of the total circulating copper in a body. It also performs various functions, for example, carrying copper to internal tissues, promoting aromatic amine oxidase activation and antioxidation, eliminating free radicals and hydrogen peroxide ($H_2O_2$), and controlling inflammatory reaction. In general, a normal person has 20–50 mg/dl of ceruloplasmin in the serum, but Wilson's disease patients have reduced level of ceruloplasmin. Normally, ceruloplasmin has an oxidase activity and exists as a copper-containing form. Also, normal persons excrete copper efficiently and have little apoceruloplasmin without the oxidase activity inside of the body (3.3±3.1 mg/dl). In contrast, Wilson's disease patients, in spite of having the equal amount of apoceruloplasmin to that of the normal persons, have little holoceruloplasmin (2.7±2.0 mg/dl).

Therefore, it is very important to quantify the ceruloplasmin in blood, particularly holoceruloplasmin, to diagnose Wilson's disease. However, in case of neonates, the screening test is ineffective to trace any sign of the disease since they normally have a low ceruloplasmin concentration. Generally, the best time to conduct the screening test would be at an age of 2 to 5, the time the ceruloplasmin concentration becoming as high as that of adults.

The conventional method for measuring ceruloplasmin in the related art includes a method for measuring holoceruloplasmin through oxidase activity of ceruloplasmin using a serum specimen, a radial immunodiffusion assay using a polyclonal antibody, or an immunoturbidimetric assay.

However, the method for measuring ceruloplasmin by measuring oxidase activity of ceruloplasmin is not very effective since ceruloplasmin does not have its own specific substrate. Also, the radial immunodiffusion assay using a polyclonal antibody is not considered specific because the polyclonal antibody reacts to not only holoceruloplasmin but also apoceruloplasmin, Besides, the above-described methods require a large amount of blood to conduct the assays, and the sera in the blood need to be separated from the whole blood by centrifugation. Even after the sera are obtained, samples need to be frozen before carrying or storing to prevent the degradation of protein in the sera. Therefore, the methods in the related art are not the best way to perform the mass screening test in that they require extra work for collecting, carrying and storing the specimen. Since the number of the specimen obtained at once is limited, a nationwide screening test requiring a large number of the specimen could not be carried out with the conventional methods.

BRIEF DESCRIPTION OF THE DRAWINGS

These and other feature of this invention will now be described with reference to the drawings of preferred embodiments which are intended to illustrate and not to limit the invention.

DETAILED DESCRIPTION OF THE PREFERRED EMBODIMENT

SUMMARY OF THE INVENTION

Figure 1:
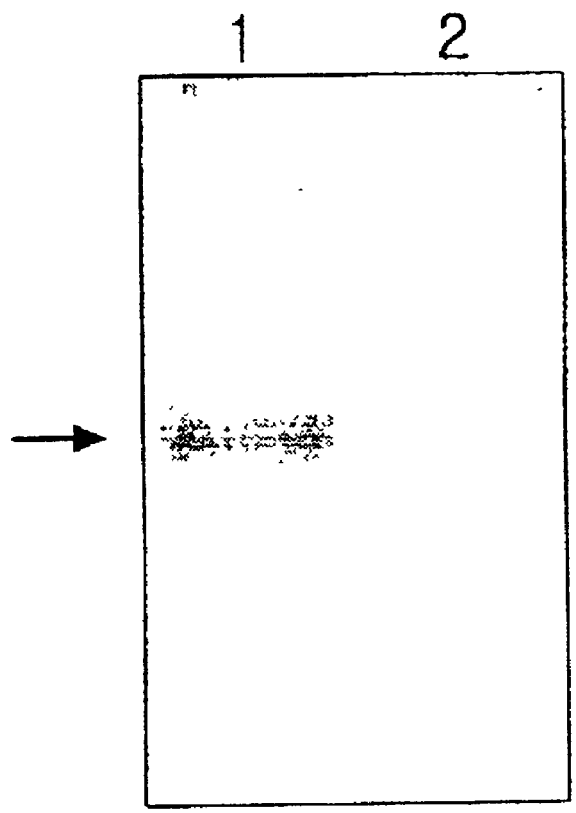
FIG. 1 shows 10 μg of purified ceruloplasmin and the same volume of hybridoma supernatant reacted together at 37° C. for 30 minutes, and electrophoresed using nonparametric polyacrylamide gel at 4° C. After the electrophoresis, the sodium acetate (pH 5.7) containing 1 mg/ml of p-phenylenediamine dyed over the gel at 37° C. for two hours to confirm the oxidase activity of ceruloplasmin, and was decolorized using 50% ethanol. Lane 1=purified ceruloplasmin; Lane 2=ceruloplasmin with a ceruloplasmin specific antibody.

It is, therefore, an object of the present invention to provide a method for measuring holoceruloplasmin concentration in a blood spot using a standard curve obtained by either an enzyme-linked immunosorbent assay (ELISA) or a dissociation-enhanced time-resolved fluoroimmunoassay employing a specific polyclonal antibody and a monoclonal antibody of holoceruloplasmin.

An another object of the present invention to provide a method for making an early diagnosis of Wilson's disease through a quantitative analysis of holoceruloplasmin in blood spot based on a sandwich ELISA method using two antibodies, for example, two monoclonal antibodies, one monoclonal antibody and one polyclonal antibody or two polyclonal antibodies. One of two antibodies recognize a epitope that plays an important role for the oxidase activity of holoceruloplasmin and the other recognize other epitopes in the same holoseruloplasmin molecule.

It is still another object of the present invention to provide a method for manufacturing a ceruloplasmin-specific polyclonal antibody using a serum produced from a rabbit immunized purified human ceruloplasmin containing holoceruloplasmin.

It is still another object of the present invention to provide a method for manufacturing a ceruloplasmin-specific monoclonal antibody using a hybridoma cell line obtained through fusion of mouse spleen cells with myeloma cells, selection and cultivation of fused spleen cells to produce an monoclonal antibody, and the spleen cells were obtained from an immunized mouse with the purified ceruloplasmin containing the holoceruloplasmin.

It is still another object of the present invention to provide a method for obtaining an absorbance standard curve according to a sandwich method of an enzyme-linked immunosorbent assay by applying a ceruloplasmin-specific polyclonal antibody and a ceruloplasmin-specific monoclonal antibody conjugated with horseradish peroxidase, respectively to a standard blood spot and a control reference blood spot manufactured.

It is still another object of the present invention to provide a method for obtaining an fluorescence standard curve according to a sandwich method of a dissociation-enhanced time-resolved fluoroimmunoassay by applying a ceruloplasmin-specific polyclonal antibody and a ceruloplasmin-specific monoclonal antibody conjugated with europium, respectively to a standard blood spot and a control reference blood spot manufactured.

It is still another object of the present invention to provide a diagnostic reagent for Wilson's disease and a screening kit of the same in order to measure holoceruloplasmin concentration in a blood spot using a standard concentration curve obtained through an enzyme-linked immunosorbent assay or a dissociation-enhanced time-resolved fluoroimmunoassay employing a holoceruloplasmin-specific polyclonal antibody and a holoceruloplasmin-specific monoclonal antibody, a manufacturing method of a standard blood spot and a control reference blood spot,.

It is still another object of the present invention to provide a new method of a quantitative analysis of copper-containing holoceruloplasmin based on an enzyme-linked immonosorbent assay or a dissociation-enhanced time-resolved fluoroimmunoassay on a blood spot obtained from a child at an age of 1 to 7 that is collected using a blood filter paper.

Ultimately, the present invention allows an early detection of Wilson's disease through a quantitative analysis of holoceruloplasmin extracted from a blood spot by the enzyme-linked immunosorbent assay or a dissociation-enhanced time-resolved fluoroimmunoassay. Especially, the present invention employs a blood spot that is easy to collect, carry and store in order to be able to measure a large number of specimens at once.

Since previously described those two methods are the world-widely accepted main methods for diagnosis kits, inventors include these two.

To achieve the above objects, the inventors developed a method for measuring holoceruloplasmin concentration in a blood spot using enzyme-linked immunosorbent assay of the present invention, the method comprising the steps of:

manufacturing a ceruloplasmin-specific polyclonal antibody;

manufacturing a ceruloplasmin-specific monoclonal antibody;

conjugating horseradish peroxidase to the ceruloplasmin-specific polyclonal antibody and the ceruloplasmin-specific monoclonal antibody;

manufacturing a standard blood spot and a control reference blood spot by adding a purified ceruloplasmin solution containing holoceruloplasmin to a ceruloplasmin-free blood to the constant concentration;

obtaining an absorbance standard concentration curve based on the standard blood spot and the control reference blood spot using the ceruloplasmin-specific polyclonal antibody and the ceruloplasmin-specific monoclonal antibody; and measuring holoceruloplasmin concentration in a blood spot of a patient according to the standard concentration curve through an enzyme-linked immunosorbent assay.

In addition, the present invention provides a method for measuring holoceruloplasmin concentration in a blood spot according to the dissociation-enhanced time-resolved fluoroimmunoassay of the present invention, the method comprising the steps of:

manufacturing a ceruloplasmin-specific polyclonal antibody;

manufacturing a ceruloplasmin-specific monoclonal antibody;

conjugating europium ($Eu^{3+}$) to the ceruloplasmin-specific polyclonal antibody and the ceruloplasmin-specific monoclonal antibody;

manufacturing a standard blood spot and a control reference blood spot by adding a purified ceruloplasmin solution containing holoceruloplasmin to a ceruloplasmin-free blood to the constant concentration;

obtaining an fluorescence standard concentration curve based on the standard blood spot and the control reference blood spot using the ceruloplasmin-specific polyclonal antibody and the ceruloplasmin-specific monoclonal antibody; and measuring holoceruloplasmin concentration in a blood spot from a patient according to the fluorescence standard concentration curve through a dissociation-enhanced time-resolved fluoroimmunoassay.

The ceruloplasmin-specific polyclonal antibody acts as an antigen and it is manufactured by immunizing a rabbit with purified ceruloplasmin containing holoceruloplasmin as an antigen. On the other hand, the ceruloplasmin-specific polyclonal antibody is manufactured by immunizing a mouse with purified ceruloplasmin containing holoceruloplasmin as an antigen in order to obtain spleen cells that produce antibodies. The spleen cells are fused with myeloma cells Sp2/0-Ag14 according to a conventional fusion method, and the fused cells are cultured in a HAT-selecting media. Then, hybridoma cells that produce antibodies are selected by applying the enzyme-linked immonosorbent assay, and monoclonal hybridoma cells are obtained by applying a limiting dilution method.

The culture supernatant containing the monoclonal antibody secreted from the hybridoma cells is reacted with ceruloplasmin, which reaction being important in that it neutralizes oxidase activity of holoceruloplasmin. In this way, hybridoma cell clones producing a holoceruloplasmin-specific antibody are selected.

In addition, the monoclonal antibody and the polyclonal antibody were conjugated with horseradish peroxidase to prepare antibodies necessary for the enzyme-linked immunosorbent assay, and with europium to prepare antibodies necessary for the dissociation-enhanced time-resolved fluoroimmunoassay.

The method for measuring holoceruloplasmin according to the enzyme-linked immonosorbent assay or the dissociation-enhanced time-resolved fluoroimmunoassay is comprised the steps of: manufacturing blood free of ceruloplasmin; manufacturing the standard blood spot and the control reference blood spot by adding purified ceruloplasmin containing the holoceruloplasmin to the blood at the constant concentration; and obtaining the standard curve based on the sandwich method using the standard blood spot and antibodies to measure holoceruloplasmin concentration in a specimen obtained from a Wilson's disease patient and a normal person, respectively.

A preferred embodiment of the present invention will now be described. It is also to be understood that the embodiment is provided for the purpose of illustration not limiting the scope of the present invention.

EXAMPLE 1

Manufacture of a Ceruloplasmin-specific Polyclonal Antibody

In the example, purified human ceruloplasmin containing holoceruloplasmin was purchased from Sigma Co., in America. In order to produce an antigen specific polyclonal antibody, 400 $\mu$l of purified ceruloplasmin that had been dissolved in a phosphate-buffered saline at the concentration of 1 mg/ml was emulsified with the same amount of Freund's adjuvant purchased from BRL Co., then the resultant was injected under the skin of a rabbit three times at 14-day intervals. Fourteen days after the last injection, 400 $\mu$l of purified ceruloplasmin that had been dissolved in a phosphate-buffered saline at the concentration of 1 mg/ml was injected to the rabbit through the ear vein, and seven days later, the blood of the rabbit was collected in accordance to a cardiac puncture method. The collected blood was left at room temperature for 30 minutes and 4° C. overnight to be completely condensed. Then, the condensed blood was centrifuged and serum was collected from the pure part of the solution. To this solution, ammonium sulfate was added, thereby making the final concentration of the solution be 40% for precipitating antibody. Later, the precipitate was dialyzed in 5L of phosphate-buffered saline (pH 7.0) for overnight and the antibody was purified by DEAE Affi-Gel Blue gel manufactured by Bio-Rad Co.

EXAMPLE 2

Manufacture of Ceruloplasmin-specific Monoclonal Antibody

In order to manufacture the monoclonal antibody of the present invention 100 $\mu$l of purified ceruloplasmin having the concentration of 1 mg/ml was emulsified with the same amount of Freund's adjuvant, and the resultant was injected to the abdomen of a BALB/c mouse at an age of 6 to 8 weeks for three times at 14-day intervals. After confirming that ceruloplasmin antibodies were produced after the last injection, 100 $\mu$g of ceruloplasmin dissolved in a phosphate-buffered saline was immunized in two weeks. Three days later, spleen cells extracted from the mouse were mixed with Sp2/0-Ag 14 myeloma cells at the ratio of 10:1. The mixture was left in polyethyleneglycol 1500 solution for 3 minutes to proceed cell fusion, and centrifuged at 1,200 rpm for 8 minutes to obtain cell precipitates. Then, the precipitates were floated on HAT/RPMI-1640 medium containing 10% fetal calf serum to make 3.5×10$^6$ cells per milliliter, and distributed to 96-well plates by 0.1 ml per well for culture in a 5% $CO_2$ culture fluid at 37° C. Three days later, the HAT/RPMI-1640 medium containing 10% fetal calf serum was added again to each well by 0.1 ml every four days, and approximately half of the medium was replaced with a fresh medium.

Following the HAT selection, the enzyme-linked immonosorbent assay was used to find out if the hybridoma cells successfully produced antibodies as intended. That is, 0.1 $\mu$g/ml of the ceruloplasmin used for immunization as aforementioned was diluted in 0.01 M carbonate-bicarbonate pH9.6, and 50 $\mu$l of the diluted solution was put into each well, which was later coated overnight at 4° C. Then, it was washed by PBST (phosphate-buffered saline, 0.05% Tween 20) three times, and reacted with 1% albumin at room temperature for two hours for blocking. Particularly, 50 $\mu$l of the culture soup of the cells was put into each well for another two-hour reaction and washed by PBST. A secondary antibody, biotin conjugated anti-mouse immunoglobulin antibody, where biotin was attached, was 1:1000 diluted in 1% BSA-PBST to make the final concentration of 1 $\mu$g/ml, and 50 $\mu$l thereof was additionally put into each well for reaction at 37° C. for one hour. The PBST was again used for cleansing the mixture in each well three times. Next, 50 $\mu$l of streptavidin-horseradish peroxidase diluted in 1% BSA-PBST by 1000 times was put into each well for another reaction at 37° C. for 30 minutes and cleansed by PBST four times. As for a substrate for an enzyme reaction, 50 $\mu$l of tetra-methylbenzidine (TMB) solution was put into each well for a reaction at room temperature. Following the reaction, 2N-sulfuric acid was added to stop the reaction, and absorbance of the resultant was measured by ELISA reader at a wavelength of 450 nm. When it was observed that ceruloplasmin antibody was produced, the cells obtained from the wells that showed a positive reaction went through the subcloning three times by the limiting dilution method until each well has 0.3 cell, and was cultured to obtain hybridoma cells that produce anti ceruloplasmin monoclonal antibody.

EXAMPLE 3

Confirmation of Ceruloplasmin Oxidase Activity Neutralization by Antibody

The mixture of 10 $\mu$g of purified ceruloplasmin and the same volume of hybridoma supernatant was reacted together at 37° C. for 30 minutes, and electrophoresed using non-parametric polyacrylamide gel at 4° C. After the electrophoresis, the sodium acetate (pH 5.7) containing 1 mg/ml of p-phenylenediamine dyed over the gel at 37° C. for two hours to confirm the oxidase activity of ceruloplasmin, and was decolorized using 50% ethanol (FIG. 1).

As shown in FIG. 1, the purified ceruloplasmin oxidized p-phenylenediamin by self-oxidase activity and formed a purple band. On the other hand, in the mixed solution of ceruloplasmin with a ceruloplasmin-specific antibody did not form the purple band since the antibody neutralized the oxidase acitivity of ceruloplasmin. Therefore, it is known that the monoclonal antibody manufactured in Example 2 shares its characteristics only with holoceruloplasmin having an oxidase activity.

EXAMPLE 4

Purification of Holoceruloplasmin-specific Monoclonal Antibody

Hybridoma cells producing the holoceruloplasmin-specific monoclonal antibody selected from Example 3 were cultured in T75 flask containing RPMI medium containing 10% fetal bovine serum and cultured in 5% $CO_2$ incubator at 37° C. for 7 days. Later, the cells were centrifuged to obtain supernatant, and ammonium sulfate was added to the culture fluid, thereby making the final concentration of the solution be 50% for precipitating antibody. Then, the solution was dialyzed in 5L of phosphate-buffered saline (pH 7.0) for overnight and the antibody was purified by DEAE Affi-Gel Blue gel.

EXAMPLE 5
Manufacture of Anti-Ceruloplasmin Antibody Conjugated with Horseradish Peroxidase 5 mg of the purified antibody obtained from Examples 1 and 4 and 5 mg of horseradish peroxidase were dialyzed in 0.1M phosphate buffer (pH 6.8) for overnight. Additionally added was glutaraldehyde solution that had been diluted by 0.1M phosphate-buffered saline until the final concentration becomes 0.1%. While slowly stirring the mixture for three hours at room temperature, 2M glycin was added to make the final concentration of 0.1M and left aside for two hours. The mixture was again dialyzed in phosphate-buffered saline for overnight and glycerol was finally added at the same volume with the mixture obtained from 30-minute centrifugation at 10,000 g, and the resultant was stored at −20° C.

EXAMPLE 6
Manufacture of Anti-Ceruloplasmin Antibody Conjugated with Europium 1 mg of the pure antibody obtained from Examples 1 and 4 was dialyzed in 0.1M sodium carbonate buffer (pH 9.3) for overnight, and condensed until the final concentration of 4 mg/ml. 250 µl of the antibody was slowly added to 0.2 mg of chelated europium $N^1$-(p-isothiocyanate benzyl)-diethylentriamine-$N^1$, $N^2$, $N^3$, $N^3$-tetra acetate (DTTA), and the reaction was continued at 4° C. for overnight. Then, the resultant was gel filtered using Superdex 200 column (distributed by Amersham Co.) and TSA buffer (50 mmol/L Tris-HCl (pH 7.8), 0.9% of NaCl, 0.0% of Sodium azide). Later, albumin was added to make the final concentration of 0.1% and the final resultant was stored at −20° C.

EXAMPLE 7
Manufacture of Ceruloplasmin-free Blood

The blood was centrifuged at 3,000 rpm for 10 minutes and plasma in the upper layer was removed. After adding phosphate-buffered saline, the centrifugation was repeated using the same method. The blood without plasma was then washed by phosphate-buffered saline for nine times using the same centrifugation method. The supernatant was discarded and ceruloplasmin-free red blood cells (RBCs) were obtained.

EXAMPLE 8
Manufacture of Standard Blood Spot

To the blood without ceruloplasmin obtained from Example 6, added was ceruloplasmin with known concentration to decide a range of standard concentration. Here, the concentrations of standard ceruloplasmin are 0 mg/dl, 1 mg/dl, 5 mg/dl, 20 mg/dl and 50 mg/dl for enzyme-linked immunosorbent assay and 0 mg/dl, 1 mg/dl, 5 mg/dl, 10 mg/dl, 20 mg/dl and 30 mg/dl for dissociation-enhanced time-resolved fluoroimmunoassay. In order to manufacture standard blood spot, the blood of Example 6 and ceruloplasmin solutions with known concentrations were mixed together at the ratio of 1:1, and the original hematocrit was adjusted finally. Therefore, when each standard concentration solution is manufactured, ceruloplasmin was doubly condensed and mixed with the blood plasma obtained from Example 7. Later, the mixture was dropped on filter paper, which was dried at room temperature for overnight.

EXAMPLE 9
Manufacture of Control Reference Blood Spot

The same procedure of Example 8 was repeated except that the control ceruloplasmin concentrations are 3 mg/dl (1.40–4.80), 7 mg/dl (5.0–9.0) and 15 mg/dl (10.5–19.5). Similar to the method for manufacturing the standard blood spot, the blood and ceruloplasmin with the known concentration were mixed at the ratio of 1:1. Later, the mixture was spotted on filter paper and it was dried at room temperature for overnight.

EXAMPLE 10
Measurement of Ceruloplasmin from Blood Spot According to Enzyme-linked Immunosorbent Assay (Sandwich Method of Monoclonal Antibody-Monoclonal Antibody)

In order to measure the amount of ceruloplasmin in a blood spot, holoceruloplasmin-specific monoclonal antibody obtained from Examples 2 and 4 was diluted by 0.05M carbonate-bicarbonate buffer to 2 µg/ml of concentration. 100 µl of diluted antibody was put into each well and coated over at 4° C. for overnight. Then, it was washed by phosphate-buffered saline containing 0.05% Tween 20 four times and reacted with phosphate-buffered saline containing 3% albumin at room temperature for 5–8 hours. After another cleansing according to the above, 1.5 mm diameter of punched blood spot was put into each well. Here, 100 µl of an eluent, phosphate-buffered saline containing 1% albumin was added to each well enough to immerse the blood spots and reacted together at 4° C. for overnight. After removing the blood spots, the well was washed by phosphate-buffered salin containing 0.05% Tween 20 four times. Then, the bounded ceruloplasmin was reacted with 100 µl of the secondary monoclonal antibody conjugated with horseradish peroxidase of Example 5, prepared by diluting at the ratio of 1:500 with the secondary monoclonal antibody and phosphate-buffered saline containing 1% albumin and 0.05% Tween 20 for 90 minutes, at room temperature. Again, the antibody was cleansed by phosphate buffer salin containing 0.05% Tween 20 six times. As for a substrate for an enzyme reaction, 100 µl of TMB solution was added to each well for the reaction at room temperature for 15 minutes, and later, the reaction was stopped by adding 100 µl of 1N-hydrochloric acid. The measurement of absorbance was accomplished at a wavelength of 450 nm using ELISA reader.

EXAMPLE 11
Measurement of Ceruloplasmin from Blood Spot According to Dissociation-enhanced Time-Resolved Fluoroimmunoassay (Sandwich Method of Monoclonal Antibody-Monoclonal Antibody)

In order to measure the amount of ceruloplasmin in a blood spot, anti holoceruloplasmin-specific monoclonal antibody obtained from Examples 2 and 4 was diluted by 0.05M carbonated bicarbonate buffer at 2 µg/ml. 100 µl of diluted antibody was put into each well and coated over at 4° C. for overnight. Then, it was washed by 50 mmol/L of Tris-HCl (pH 7.8) buffer containing 0.1% Tween 20 and 0.9% of NaCl four times and reacted with Tris-HCl (pH 7.8) buffer containing 3% albumin at room temperature for 5–8 hours. After another washing according to the above, 1.5 mm diameter of punched blood spot was put into each well. Here, 100 µl of an eluent, DELFIA assay buffer (distributed by Wallac Co.), was added to each well enough to immerse the blood spots and reacted together at 4° C. for overnight. After removing the blood spots, the wells were washed by Tris-HCl (pH 7.8) buffer containing 0.1% Tween 20 and 0.9% NaCl. Then, the bounded ceruloplasmin in the cell was reacted with the secondary monoclonal antibody conjugated with europium of Example 6 diluted by DELFIA assay buffer to make the concentration of 250 ng/ml for 90 minutes at room temperature. Again, the wells were washed by Tris-HCl (pH 7.8) containing 0.1% Tween 20 and 0.9% NaCl four times. Finally, 200 µl of DELFIA enhancement solution (distributed by Wallac Co.) was added to each well and two minutes later, copy number of europium was measured using a time-resolved fluorometry.

EXAMPLE 12
Measurement of Ceruloplasmin from Blood Spot According to Enzyme-linked Immunosorbent Assay (Sandwich method of Monoclonal Antibody-Polyclonal Antibody)

The same procedure of Example 10 was employed in order to measure the amount of ceruloplasmin in the blood spot except that the polyclonal antibody conjugated with horseradish peroxidase obtained from Examples 1 and 5 was used for the secondary antibody.

EXAMPLE 13
Measurement of Ceruloplasmin from Blood Spot According to Dissociation-enhanced Time-resolved Fluoroimmunoassay (Sandwich method of Monoclonal Antibody-Polyclonal Antibody)

The same procedure of Example 11 was employed in order to measure the amount of ceruloplasmin in the blood spot except that the polyclonal antibody conjugated with europium obtained from Examples 1 and 6 was used for the secondary antibody.

EXAMPLE 14
Measurement of Ceruloplasmin from Blood Spot According to Enzyme-linked Immunosorbent Assay (Sandwich method of Polyclonal Antibody-Polyclonal Antibody)

The same procedure of Example 10 was employed in order to measure the amount of ceruloplasmin in the blood spot except that the polyclonal antibody obtained from Example 1 was used for the coating antibody and polyclonal antibody conjugated with horseradish peroxidase obtained from Examples 1 and 5 was used for the secondary antibody, respectively.

EXAMPLE 15
Measurement of Ceruloplasmin from Blood Spot According to Dissociation-enhanced Time-resolved Fluoroimmunoassay (Sandwich method of Polyclonal Antibody-Polyclonal Antibody)

The same procedure of Example 11 was employed in order to measure the amount of ceruloplasmin in the blood spot except that the polyclonal antibody obtained from Example 1 was used for the coating antibody and polyclonal antibody conjugated with europium obtained from Examples 1 and 6 was used for the secondary antibody, respectively.

Figure 2:
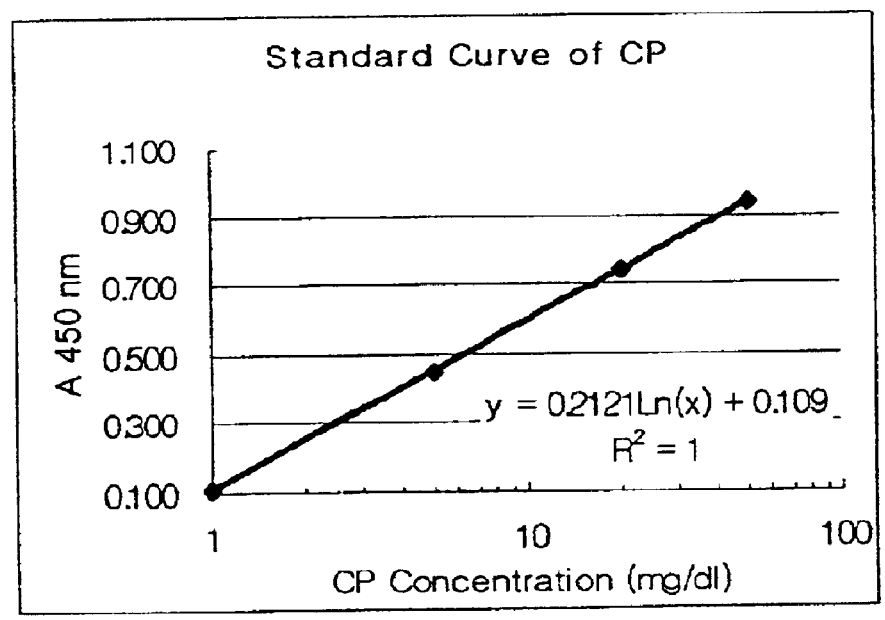
FIG. 2 shows a standard curve for ceruloplasmin concentration obtained by the method of Example 10.

EXAMPLE 16
Quantitative Analysis of Ceruloplasmin on Normal Controls and Wilson's disease Patients According to Enzyme-linked Immunosorbent Assay Blood was collected from 5 normal controls and 12 of Wilson's disease patients in order to make blood spots. After drying the blood spots overnight, the ceruloplasmin concentration was measured based on the standard concentration curve according to the method explained in Example 10 (FIG. 2).

Figure 3:
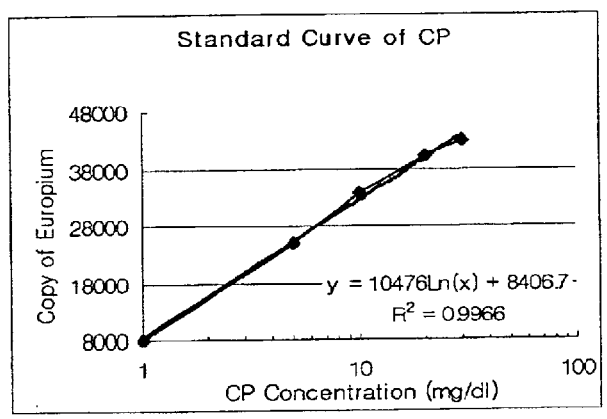
FIG. 3 shows a standard curve for ceruloplasmin concentration obtained by the method of Example 11.

EXAMPLE 17
Quantitative Analysis of Ceruloplasmin on Normal Controls and Wilson's disease Patients According to Dissociation-enhanced Time-resolved Fluoroimmunoassay Blood was collected from 5 normal controls and 12 of Wilson's disease patients in order to make blood spots. After drying the blood spots overnight, the ceruloplasmin concentration was measured based on the standard concentration curve according to the method explained in Example 11 (FIG. 3).

Figure 4:
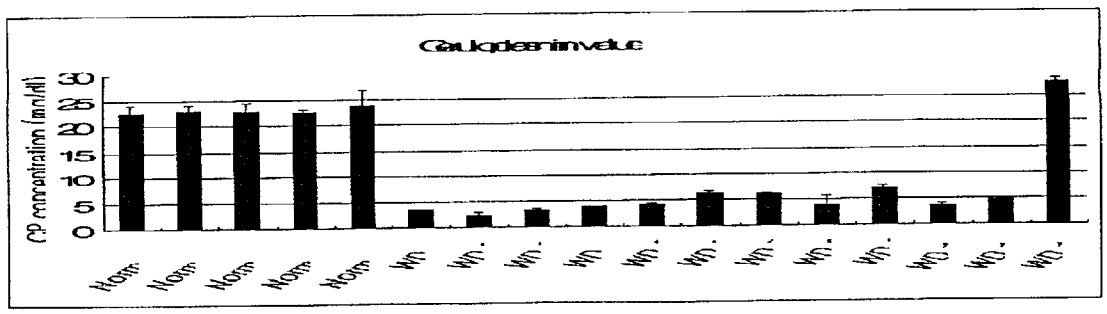
FIG. 4 shows ceruloplasmin concentration in 5 normal individuals and 12 Wilson's disease patients.

As shown in FIG. 4, the ceruloplasmin concentration of the Wilson's disease patient was noticeably lower than that of the normal controls, which proves that the diagnosis reagent of the present invention is very effective to diagnose Wilson's disease at an early stage of clinical course. However, as in the case of the Wilson's disease patient (WD 12) illustrated in FIG. 4, 5% of patients in Wilson's disease would exhibit the normal ceruloplasmin concentration. In such cases, early diagnosis could be difficult with this method.

In conclusion, the present invention provides the method of quantitative analysis for holoceruloplasmin in the blood spot collected on filter papers from the children at an age of 1 to 7 using the enzyme-linked immonosorbent assay or the dissociation-enhanced time-resolved fluoroimmunoassay, and could be used as screening kit for an early diagnosis of Wilson's disease. According to the present invention, only a few drops of blood punctured by lancet are enough to diagnose the disease, making more efficient as a mass screening measured than conventional assay such as radial immunodiffusion assay and immunoturbidimetric assay.

The Wilson's disease diagnosis reagent and the Wilson's disease diagnosis kit of the present invention make it possible to measure holoceruloplasmin concentration in the blood spot based on the standard concentration curve obtained through the enzyme-linked immunosorbent assay or the dissociation-enhanced time-resolved fluoroimmunoassay using the holoceruloplasmin-specific polyclonal antibody, a holoceruloplasmin-specific monoclonal antibody, a standard blood spot and a control reference blood spot. Accordingly, since the method of the present invention is very convenient to collect, carry and store the specimen required for the mass screening, it is more possible to analyze the large number of samples at once and it is now possible that the mass screening of Wilson's disease can be applied with one invented method.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A method of measuring a holoceruloplasmin concentration in a blood spot comprising:
   a) binding the holoceruloplasmin eluted from a blood spot to a holoceruloplasmin-specific polyclonal antibody and a holoceruloplasmin-specific monoclonal antibody: and
   b) measuring a holoceruloplasmin concentration in the blood spot based on an absorbance standard curve obtained through an assay using a holoceruloplasmin-specific polyclonal antibody and a holoceruloplasmin-specific monoclonal antibody.

2. The method of claim 1, wherein the blood spot is collected using a blood filter paper.

3. The method of claim 1, wherein the ceruloplasmin-specific polyclonal antibody is manufactured from the serum that is obtained by a rabbit immunized with purified human ceruloplasmin containing the holoceruloplasmin.

4. The method of claim 1, wherein the ceruloplasmin-specific monoclonal antibody is manufactured from a hybridoma cell line obtained through fusion of mouse spleen cells with myeloma cells, selection and cultivation of the fused spleen cells to produce a monoclonal antibody, and wherein the spleen cells were obtained by immunization of a mouse with purified ceruloplasmin containing holoceruloplasmin.

5. A method of measuring a holoceruloplasmin concentration in a blood spot according to an enzyme-linked immunosorbent assay, the method comprising the steps of:
- manufacturing a ceruloplasmin-specific polyclonal antibody;
- manufacturing a ceruloplasmin-specific monoclonal antibody;
- conjugating horseradish peroxidase on the ceruloplasmin-specific polyclonal antibody and the ceruloplasmin-specific monoclonal antibody;
- manufacturing a standard blood spot and a control reference blood spot by removing a ceruloplasmin from a blood sample and adding a purified ceruloplasmin solution containing a holoceruloplasmin at a constant concentration to the blood sample;
- drawing out an absorbance standard curve based on the standard blood spot and the control reference blood spot using the ceruloplasmin-specific polyclonal antibody and the ceruloplasmin-specific monoclonal antibody; and
- measuring a holoceruloplasmin concentration in a blood spot of a patient using the standard curve through an enzyme-linked immunosorbent assay.

6. A method of measuring a holoceruloplasmin concentration in a blood spot according to a dissociation-enhanced time-resolved fluoroimmunoassay, the method comprising the steps of:
- manufacturing a ceruloplasmin-specific polyclonal antibody;
- manufacturing a ceruloplasmin-specific monoclonal antibody;
- conjugating with europium on the ceruloplasmin-specific polyclonal antibody and the ceruloplasmin-specific monoclonal antibody;
- manufacturing a standard blood spot and a control reference blood spot by removing a ceruloplasmin from a blood sample and adding a purified ceruloplasmin solution containing a holoceruloplasmin at a constant concentration to the blood sample;
- drawing out an fluorescence standard curve based on the standard blood spot and the control reference blood spot using the ceruloplasmin-specific polyclonal antibody and the ceruloplasmin-specific monoclonal antibody; and
- measuring a holoceruloplasmin concentration in a blood spot of a patient using the standard curve through a dissociation-enhanced time-resolved fluoroimmunoassay.

7. The method of claim 5, wherein the patient has Wilson's disease.

8. The method of claim 5, wherein the step of removing the ceruloplasmin in the blood is made using a phosphate-buffered saline.

9. The method of claim 5, wherein the standard blood spot and the control reference blood spot are manufactured by adding a ceruloplasmin with a known concentration to the blood without the ceruloplasmin.

10. The method of claim 9, wherein the known concentration of the ceruloplasmin has at least 3 different values.

11. The method of claim 5, comprising a further step of screening an antibody for neutralizing an oxidase activity of the holoceruloplasmin at the step of manufacturing the ceruloplasmin-specific monoclonal antibody.

12. The method of claim 5, comprising a further step of purifying the antibody after the step of manufacturing the ceruloplasmin-specific monoclonal antibody.

13. A Wilson's disease screening kit reagent, comprising a holoceruloplasmin-specific polyclonal antibody, a holoceruloplasmin-specific monoclonal antibody, a standard blood spot, and a control reference blood spot.

14. A Wilson's disease screening kit, for measuring a holoceruloplasmin concentration in a blood spot based on an absorbance standard curve obtained through an enzyme-linked immunosorbent assay using a holoceruloplasmin-specific polyclonal antibody, a holoceruloplasmin-specific monoclonal antibody, a standard blood spot, and a control reference blood spot.

15. A Wilson's disease screening kit, for measuring a holoceruloplasmin concentration in a blood spot based on a fluorescence standard curve obtained through a dissociation-enhanced time-resolved fluoroimmunoassay using a holoceruloplasmin-specific polyclonal antibody, a holoceruloplasmin-specific monoclonal antibody, a standard blood spot, and a control reference blood spot.

16. A method of diagnosing Wilson's disease using the screening kit of claim 14.

17. The method of claim 1, wherein the assay is an enzyme-linked immunosorbent assay and the concentration of holoceruloplasmin is based upon an absorbance standard curve.

18. The method of claim 1, wherein the assay is dissociation-enhanced time-resolved fluoroimmunoassay and the concentration of holoceruloplasmin is based upon a fluorescence standard curve.

19. The method of claim 6, wherein the patient has Wilson's disease.

20. The method of claim 6, wherein the step of removing the ceruloplasmin in the blood is made using a phosphate-buffered saline.

21. The method of claim 6, wherein the standard blood spot and the control reference blood spot are manufactured by adding a ceruloplasmin with a known concentration to the blood without the ceruloplasmin.

22. The method of claim 21, wherein the known concentration of the ceruloplasmin has at least 3 different values.

23. The method of claim 6, comprising a further step of screening an antibody for neutralizing an oxidase activity of the holoceruloplasmin at the step of manufacturing the ceruloplasmin-specific monoclonal antibody.

24. The method of claim 6, comprising a further step of purifying the antibody after the step of manufacturing the ceruloplasmin-specific monoclonal antibody.

25. A method of diagnosing Wilson's disease using the screening kit of claim 15.

26. The method of claim 17, wherein the absorbance standard curve according to the enzyme-linked immunosorbent assay is drawn out by applying the ceruloplasmin-specific polyclonal antibody and the ceruloplasmin-specific monoclonal antibody conjugated with horseradish peroxidase, respectively to a standard blood spot and a control reference blood spot.

27. The method of claim 26, wherein the enzyme-linked immunosorbent assay drawing out the absorbance standard curve is based on a sandwich method using the cerulaplasmin-specific polyclonal antibody and the ceruloplasmin-specific monoclonal antibody conjugated with horseradish peroxidase, respectively.

28. The method of claim 18, wherein the fluorescence standard curve according to the dissociation-enhanced time-resolved fluoroimmunoassay is drawn out by applying the ceruloplasmin-specific polyclonal antibody and the ceruloplasmin-specific monoclonal antibody conjugated with europium, respectively to a standard blood spot and a control reference blood spot.

29. The method of claim 28, wherein the dissociation-enhanced time-resolved fluoroimmunoassay for drawing out the fluorescence standard curve is based on a sandwich ELISA method using the ceruloplasmin specific polyclonal antibody and the ceruloplasmin-specific monoclonal antibody conjugated with europium, respectively.

* * * * *